US008229198B2

(12) United States Patent
Pfister et al.

(10) Patent No.: US 8,229,198 B2
(45) Date of Patent: Jul. 24, 2012

(54) METHOD FOR CREATING IMAGE RECORDINGS RELATING TO THE BLOOD VESSEL SYSTEM OF A PATIENT USING A VARIABLE-POSITION DETECTOR OF A DIGITAL SUBTRACTION ANGIOGRAPHY FACILITY AND ASSOCIATED FACILITY

(75) Inventors: Marcus Pfister, Bubenreuth (DE); Thomas Redel, Poxdorf (DE)

(73) Assignee: Siemens Aktiengesellschaft, München (DE)

( * ) Notice: Subject to any disclaimer, the term of this patent is extended or adjusted under 35 U.S.C. 154(b) by 776 days.

(21) Appl. No.: 12/319,517

(22) Filed: Jan. 8, 2009

(65) Prior Publication Data
US 2009/0180676 A1 Jul. 16, 2009

(30) Foreign Application Priority Data
Jan. 11, 2008 (DE) .......................... 10 2008 003 945

(51) Int. Cl.
*G06K 9/00* (2006.01)
*A61K 49/04* (2006.01)
(52) U.S. Cl. ........................................ 382/130; 424/9.4
(58) Field of Classification Search .................. 382/128, 382/130–132; 378/42, 98.12; 250/370.03, 250/370.09
See application file for complete search history.

(56) References Cited

U.S. PATENT DOCUMENTS 5,347,570 A * 9/1994 Haaks ........................ 378/98.12
6,795,524 B2 * 9/2004 Hayashi ...................... 378/98.12
7,283,614 B2 * 10/2007 Nakano et al. .............. 378/98.12
7,386,156 B2 * 6/2008 Hornegger ................... 382/130

OTHER PUBLICATIONS

Arnulf Oppelt (Editor), "Imaging Systems for Medical Diagnostics", Chapter: Perivision and peristepping; Publicis Corporate Publishing, Erlangen, 2005, pp. 369-371, Book.
Zhenyu Wu; Jian-Zhong Qian, "Real-time tracking of contrast bolus propagation in X-rayperipheral angiography", Biomedical Image Analysis, 1998. Proceedings, Volume , Issue , Jun. 26-27, 1998 pp. 164-171.
Siemens AG, Medical Solutions, AX; AXIOM Artis, Quick Guide for Special Examinations, Software Version VB30 and higher, Print No. AXA4-300.622.10.01.02, May 2006, pp. 1-74.
T. A. Sos and D. Trost, "Peripheral angiography: Contrast saving strategies in the digital age", Medicamundi, vol. 41, Issue 2, Nov. 1997; pp. 36-42.

* cited by examiner

*Primary Examiner* — Pascal M Bui Pho

(57) ABSTRACT

Method for creating image recordings of blood vessel system of a patient, comprising: after administering contrast agent an image recording is created in a first image recording region of a first position of a detector, the diffusion of the contrast agent is observed to determine a current diffusion position; the position of the detector is changed to a second position as a function of the current diffusion position; an image recording of a second image recording region of the second position of the detector is created; and a part of an image recording in the first position extending in the region between the current diffusion position and the end of the first image recording region and recorded without contrast agent is used as a mask to evaluate a locationally correlated part, recorded with contrast agent, of the image recording in the second position for digital subtraction angiography.

14 Claims, 4 Drawing Sheets

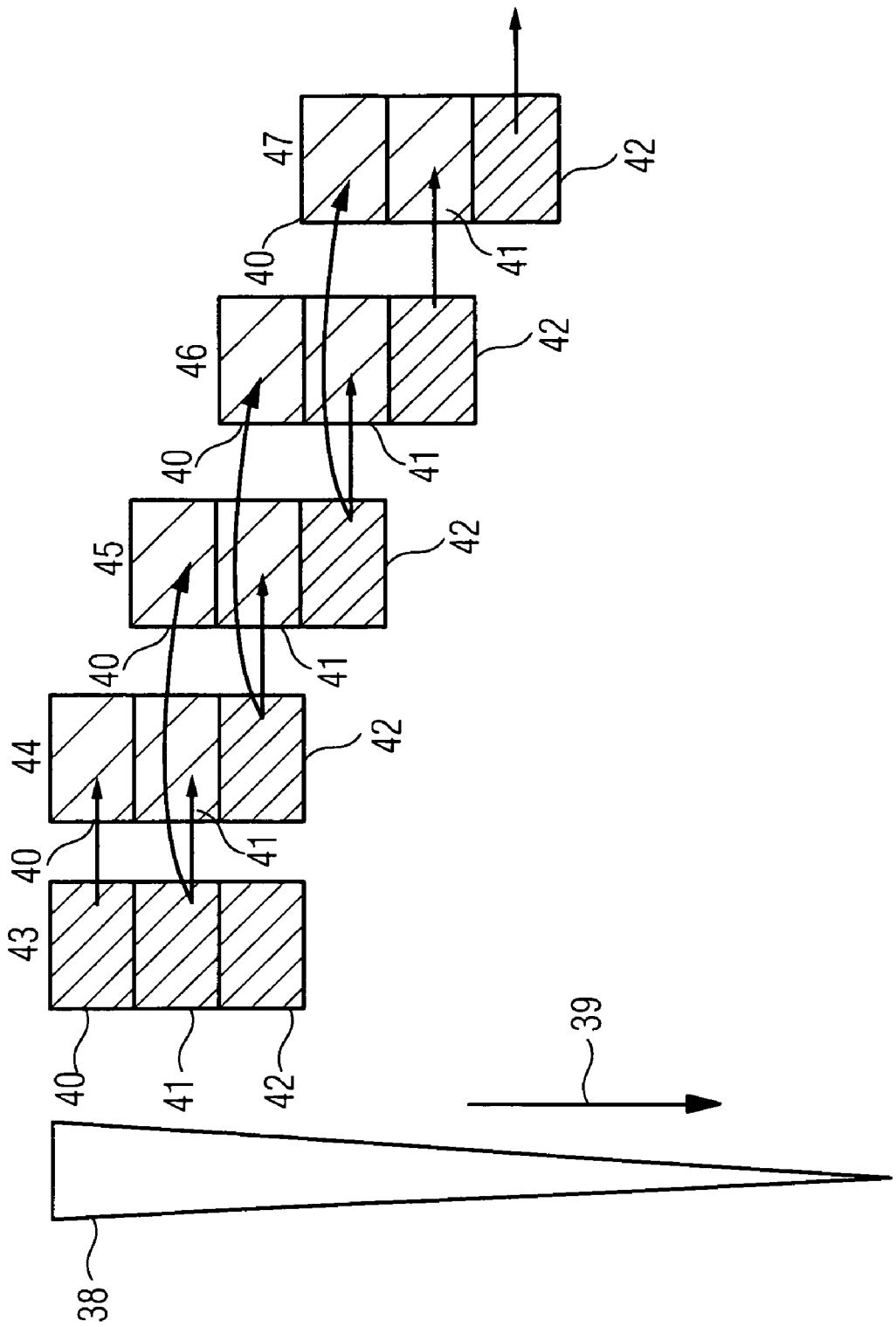

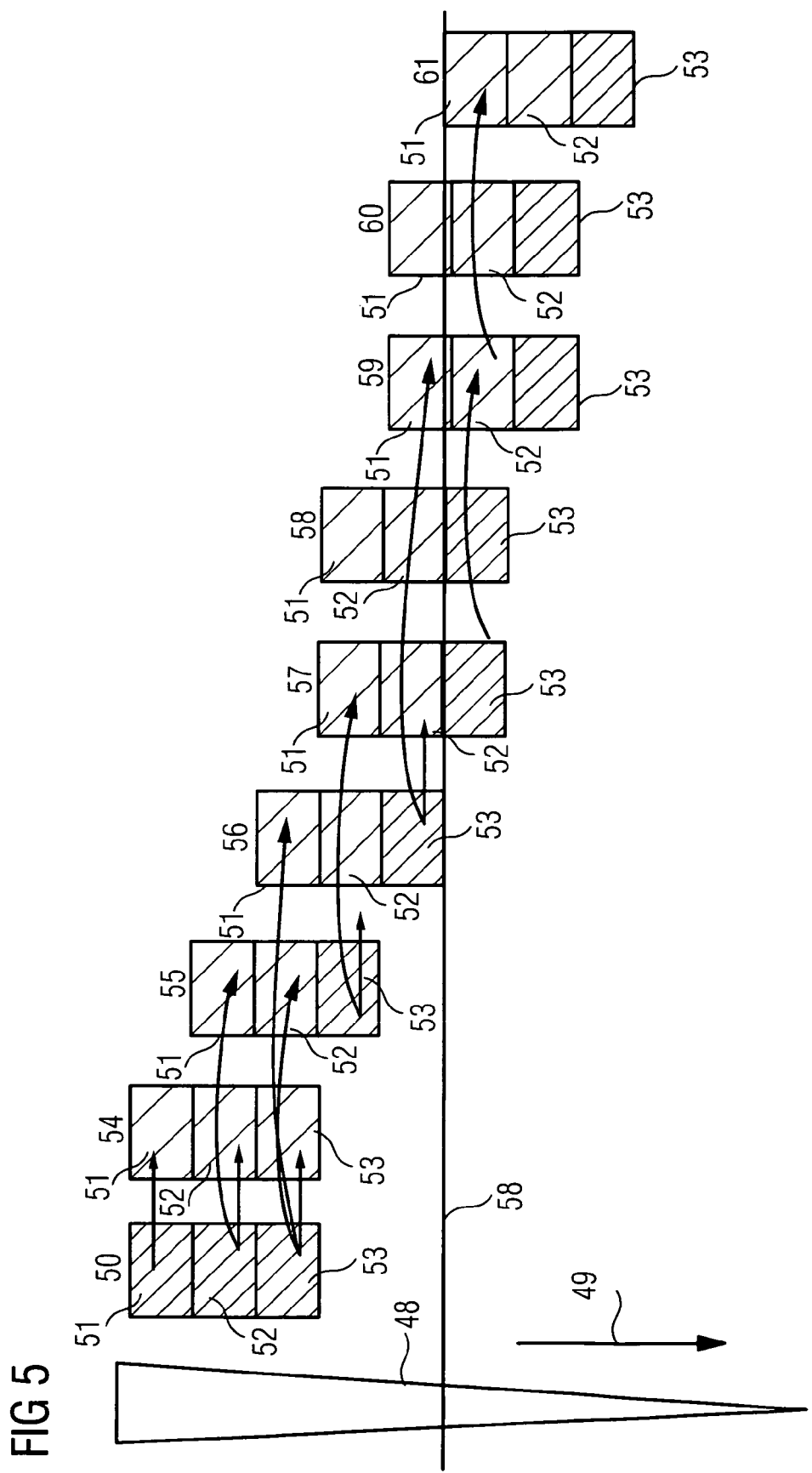

METHOD FOR CREATING IMAGE RECORDINGS RELATING TO THE BLOOD VESSEL SYSTEM OF A PATIENT USING A VARIABLE-POSITION DETECTOR OF A DIGITAL SUBTRACTION ANGIOGRAPHY FACILITY AND ASSOCIATED FACILITY

CROSS REFERENCE TO RELATED APPLICATIONS

This application claims priority of German application No. 10 2008 003 945.4 filed Jan. 11, 2008, which is incorporated by reference herein in its entirety.

FIELD OF THE INVENTION

The invention relates to a method for creating image recordings relating to the blood vessel system of a patient using a variable-position detector of a digital subtraction angiography facility and an associated digital subtraction angiography facility.

BACKGROUND OF THE INVENTION

In angiography blood vessels are displayed using diagnostic imaging methods, with a contrast agent generally being administered to the patient, in particular by means of injection, to show or emphasize the contrast in the images. Angiography methods are generally used to examine the vascular system of patients with arteriosclerosis. They allow the coronary vessels of a patient for example to be imaged so that a physician is then able to make a diagnosis.

Diseases of the vascular system, for example arteriosclerosis, are however frequently systemic diseases, i.e. patients who are examined for disease of the coronary vessels in a cardiac catheter laboratory for example, will quite probably also exhibit a peripheral manifestation of the disease, in the legs or limbs generally for example.

It is therefore in principle advantageous also to produce recordings of other body regions, for example the legs, during a cardiac examination, to enable a comprehensive assessment of the disease.

In order to record more extended, in particular longer, anatomical regions using angiography, the peripheral digital subtraction angiography method (extending to peripheral regions), also referred to as "perivision", is frequently used. Here an anatomical mask image is subtracted in each instance from a vascular image filled with contrast agent (digital subtraction angiography or DSA) in a number of recording positions covering the entire region, to obtain a visualization of the vessels alone.

The workflow required for this is however relatively time-consuming and complex. On the one hand a total of three imaging passes has to be carried out, in particular a first test pass followed by a separate mask pass and a so-called fill pass (with contrast agent in the recording region), requiring not only a considerable time outlay but also numerous user interactions to control the method.

It is also frequently standard practice during the fill pass in order to monitor the contrast agent, to trigger the further movement of a detector from one recording position to the next manually, in order thus to be able to monitor the course of the contrast agent or the diffusion of the contrast agent in the body of the patient. This requires considerable experience on the part of the operator.

SUMMARY OF THE INVENTION

The object of the invention is to specify an improved method in this respect.

To achieve this object a method is provided for creating image recordings relating to the vascular system of a patient using a variable-position detector of a digital subtraction angiography facility, having the following steps:

After administering contrast agent at least one image recording relating to the vascular system of the patient is created of a first image recording region assigned to a first position of the detector, then the diffusion of the contrast agent in a predetermined direction of the first image recording region is observed and/or defined to determine a current diffusion position, The position of the detector in the predetermined direction is changed to a second position as a function of the determination of a defined current diffusion position, At least one image recording of a second image recording region assigned to the second position of the detector is created and At least a part of an image recording created in the first position of the detector extending in the region between the defined current diffusion position and the end of the first image recording region in the predetermined direction and thus recorded without contrast agent is used as a mask to evaluate a locationally correlated part, recorded with contrast agent, of at least one image recording created in the second position of the detector for digital subtraction angiography.

Before implementing the inventive method the patient is first positioned on an examination table or couch. The starting point of a detector for example for a recording of the leg region can be established in the pelvic region for example, being correspondingly different for other recording regions. The point of origin of a corresponding coordinate system for the image recordings to be created can then be set at this starting point, with the z-axis generally and particularly for leg recordings running in the direction of the feet of the patient.

Then prior to the method a contrast agent can be administered, in particular injected. This can be controlled (fully) automatically or even manually. Optionally at least one recording can be created in the region of the starting point, in other words a first recording of a series of recordings, still without contrast agent.

After administration of the contrast agent according to the invention at least one image recording relating to the blood vessel system or specific vessels, in other words for example to the vessels or some of the vessels in the leg region, is produced with the detector in a first position, in particular in the position already used for a recording without contrast agent. This recording can thus relate for example to a first image recording region starting from the patient's pelvis in the direction of the feet.

The diffusion of the contrast agent in the body of the patient is observed in parallel with the creation of this one or number of recordings in the first detector position. This observation can take place manually, optionally taking into account image recordings (in other words more than one) created at specific time intervals or a film for the first detector position but preferably takes place in an automated manner (optionally in a supplementary manner) for example with recourse to corresponding models or using automatic image processing or image evaluation.

Inventive method implementation therefore focuses on the monitoring of the diffusion of the contrast agent in the direction in which subsequent recordings are to be produced, in other words for example when creating leg recordings starting from the pelvic region, diffusion of the contrast agent in the direction of the feet of the patient.

For the diffusion of the contrast agent in this therefore predetermined direction a current diffusion position is determined at specific time intervals or continuously or a control and/or computation facility for example determines when the current diffusion position corresponds to a predetermined diffusion position or when the contrast agent has diffused to a specific point.

The diffusion position here can be defined variously. For example a diffusion position can be reached when the contrast agent or contrast agent bolus in a single vessel reaches a specific front point of the image recording region or detector. Similarly however a current diffusion position can be deemed to be assumed for example when a specific proportion of the contrast agent has reached or flowed through a specific z-position in, optionally a number of, vessels.

The position of the detector in the predetermined direction is then changed to a second position as a function of such a determination of a specific current diffusion position. It is therefore determined for example when the contrast agent or some of the contrast agent reaches a specific front region of the image recording region or for example approximately a specific predetermined distance from the detector length, whereupon the detector position is changed. The detector is thus moved by a specific amount in the recording direction, in other words into the peripheral recording region in the example of the leg recording. It is then in a second recording position. It is advantageous to create an image recording associated with the detector advance, for example shortly before it, in the respectively previous position, in order thus to obtain a fill image (with contrast agent) of an end region or larger region of the image recording area.

One or more image recordings are again created in this second recording position of the detector, associated correspondingly with a second image recording region, which extends peripherally.

According to the invention a region of at least one image recorded in the first detector position, in which there is still no contrast agent present, in other words a front part of an image in respect of the predetermined diffusion direction of the contrast agent, is now used as a mask for evaluating a corresponding part of an image created in the second position of the detector, in which contrast agent is already present in the corresponding region, due to the continuing diffusion of the contrast agent.

This part of the first image, which could also be referred to as an image segment, may thus not be recorded with contrast agent in the corresponding vessels, in order to be able to be used as a mask. This part must therefore extend between the current diffusion position (in other words optionally starting with this position), which has resulted in the change in the position of the detector due to the flow of contrast agent, and the end of the first image recording region. This front part can expediently be the overall region from the current diffusion position or a point at a (fairly short) distance from this diffusion position in the direction of the peripheral recording region to the end of the first image recording region or correspondingly the recording surface of the detector.

According to the invention the respective front part of a recorded image, being the part of the image which contains no contrast agent, is thus used as a mask for an evaluation in the context of digital subtraction angiography for at least one subsequent image, in which the detector has moved a little further, in other words has undergone an advance.

This has the advantage that a separate mask pass is superfluous and the workflow is thus generally significantly simplified and facilitated. The mask sun can thus be omitted, as selective data from a fill pass is used for subtraction purposes.

Before contrast agent administration at least a first image recording relating to the vascular system of the patient can be created of the first image recording region assigned to the first position of the detector.

Such a first recording of the starting point, for example as the first recording of a series of recordings produced without contrast agent, can serve to optimize the recording parameters or can even be used as a mask image or a mask image for a specific region captured with this image recording for subtraction purposes for the first position of the detector. Once this recording has been created a contrast agent can be injected with automatic or manual control.

A part of an image recording created in a specific position of the detector extending in the region between the specific current diffusion position and the end of the associated image recording region in the predetermined direction and therefore recorded without contrast agent can be used as a mask for evaluating a locationally correlated part, recorded with contrast agent, of at least one image recording created after at least two further changes in the position of the detector in the then current position of the detector.

The position of the detector is moved a number of times normally, as a function of its size, to capture the entire region to be examined, for example the legs, with a part of the image, which was recorded in a specific position then being able to be used not only as a mask for a recording in a directly subsequent detector position but optionally also as a mask for parts of images recorded in the next but one or next but two detector position and so on. The only important thing here is that the recording to be used as a mask has recorded a region that overlaps with the recording created in the next, next but one, etc. position, so that locationally correlated recordings are correspondingly available.

The observation and/or definition of the diffusion of the contrast agent and/or the change in the position of the detector can be carried out automatically on the part of a control and/or computation facility of the facility for digital subtraction angiography, in particular using appropriate algorithms.

It is therefore possible in particular for automatic monitoring of the contrast agent bolus to be used (keyword "bolus tracking"). Such an, optionally fully, automated observation or monitoring of contrast agent diffusion is generally based on specific (mathematical or physical) models for diffusion behavior implemented as program means and/or image processing methods, which can be used to monitor the current diffusion flow of the contrast agent based on image recordings. Similarly the advance of the detector can be triggered or carried out in an automated manner, in particular as a function of the contrast agent reaching a specific diffusion position. For example a specific front region of the image recording region can be predetermined, for which a detector advance is triggered when the contrast agent approaches a specific distance therefrom.

According to the invention the method can advantageously be implemented in a fully automated manner on the part of a control and/or computation facility, in particular on the part of the above-mentioned control and/or computation facility of the digital subtraction angiography facility, optionally after an operator-initiated start.

This is particularly advantageous in respect of the fact that the creation of such image recordings covering a larger body region in order to allow comprehensive diagnosis of a patient is moving increasingly from the field of work of radiologists to specialists dealing with the disease in the foreground, for example cardiologists in the case of arteriosclerosis of the coronary vessels. These specialists generally do not have profound knowledge of recording methods and also want the simplest and least time-consuming procedure possible. In this instance fully automated implementation of the method is offered, in particular in the form of a "one button procedure". Of course it is equally possible for different operator interventions to be at least enabled but optionally also requested by way of a program means. For this optionally a number of operator programs can be available, allowing or requiring more or less comprehensive intervention by the operator or at least confirmation on the part of the operator at least at some points of the program run. For example a change to the acquisition parameters due to an inadequate image quality identified during image processing can require operator confirmation.

The detector and/or an image recording region can be divided into at least two virtual parts, in particular into three parts, during the implementation of the method. These parts, which can optionally also be referred to as segments etc., can be specific segments of the detector surface directly or optionally segments defined based on the image recording region. A front segment here can be the segment between a position of the contrast agent triggering an advance of the detector or a position at a specific distance from the current diffusion position and the front end of the detector or the image recording region. The remaining detector length can be divided into corresponding parts. The virtual discrete portioning, for example in the form of a division into three, allows specific different regions to be defined for the acquisition of a fill image, for bolus tracking or for a mask.

In particular one part or segment can be defined as a part of an image recording region from a specific current diffusion position or a position at a specific distance from this to the end of the corresponding image recording region in the predetermined direction and/or one part can be defined as a part of the detector from a detector point corresponding to a specific current diffusion position or a position at a specific distance from this to the end of the detector in the predetermined direction.

This procedure allows a front segment to be defined as a function of the result of the tracking or observation of the diffusion of the contrast agent, whose recording data is available as a mask for recordings in the next detector position or of the next image recording region, since there is still no contrast agent present in this front image segment.

The detector and an image recording region are advantageously divided into parts of equal size. It is thus possible to define a specific number of segments, each being of equal size. Segments of equal size are offered, as these can be used directly for subtraction in the context of digital subtraction angiography without further calculation and without the risk of error. This means that the image parts interlinked or interrelated in the context of subsequent processing, for example subtraction, are of directly corresponding size. Of course in some circumstances it is also possible to select segments of different sizes, with these different sizes then having to be taken into account during processing, in such a manner that the mask image for example actually shows the whole region required in respect of the images recorded with contrast agent and image regions from which it is to be subtracted.

The detector and/or an image recording region can be divided discretely or continuously. Discrete portioning into segments offers particularly simple processing here. Of course it is also possible to use different divisions, for example based on a continuous algorithm system.

In particular when the detector and/or an image recording region is divided into a number of parts at least one part can be used to acquire a fill image and/or at least one part can be used to observe and/or define the diffusion of the contrast agent and/or at least one part can be used to acquire a mask.

Therefore a division into three is primarily offered, with which a first part serves to acquire a fill image, in other words the image with contrast means, while the second segment is used for bolus tracking, in other words to ascertain the current diffusion of the contrast agent, while the third segment, which is thus assigned to an image recording without contrast agent, serves to acquire the mask image. In this process the image recordings are optionally created across all three segments (optionally also with repetition), so that in this instance for example the mask image would strictly speaking be a partial image of a larger recording.

It is also possible for division to take place into fewer than three parts, with one region dealing with more than one task. It is only necessary here for a recording to be created without contrast agent in a specific region, which is available as a mask for recordings in one or more subsequent detector positions.

According to the invention the position of the detector can be changed by a fraction of the number of parts, into which the detector and/or an image recording region is divided, in relation to the overall extension of the detector in the predetermined direction.

For example when the detector length or the image recording region is divided into three, in other words into three segments, the detector is advanced in each instance by a third of the detector dimension in the corresponding direction, generally the z-direction or the direction of a patient table. Generally such an advance by a fraction of the division segments is expedient, as then in the new position the recording is automatically created in a manner corresponding to the previous position with identical segment division.

The method can be implemented by changing the position of the detector in steps, until a predetermined region of the blood vessel system of the patient is recorded and/or an operator terminates implementation of the method and/or the contrast agent is no longer propagated.

Of course it is not necessary (generally) then to re-administer contrast agent, just to create an image recording in the respective new position after the detector has advanced with further bolus tracking, in order thus to be able to trigger a further advance to a subsequent position.

It is thus possible to carry out step by step recording of the entire relevant region, until the user stops acquisition or until a lack of contrast agent propagation is established as an abort criterion by bolus tracking or another criterion.

At least one recording parameter can be modified while image recordings relating to the blood vessel system of the patient are being created.

This means that during or in the course of acquisition of the image recordings one or more recording parameters can be modified, for example to improve recording quality or if requirements change. If the parameters in question are for algorithmic post-processing steps, these can be taken into account sector by sector. If the modifications cannot be corrected by way of software, such as for example changes to the shutters or a voltage present at a radiation source, in some instances it is necessary to create recordings in a parallel manner in the same detector position.

It is thus possible, in the event that at least one recording parameter is modified in at least one corresponding position of the detector, to create at least one image recording with the previous recording parameters and at least one image recording with at least one modified image parameter and correspondingly to use parts with corresponding recording parameters for the subtraction in each instance.

The procedure is therefore such that, if a shutter setting is modified for example, two recordings respectively are produced in a parallel manner with the different shutter settings or the other different parameter settings for the corresponding detector positions. Subtraction in the context of digital subtraction angiography then takes place respectively on the basis of the corresponding recordings under the respective different setting conditions. For example if the detector is divided into three segments, when the recording parameters are modified, a double recording can take place respectively in two different detector positions, in order thus to obtain the necessary data for the subtraction method.

A part of an image recording used as a mask for evaluation purposes can also be used for analysis and/or optimization of at least one image recording parameter. Thus the image information in a front detector segment can be used for example for analysis and subsequent optimization of the recording parameters, for example the shutter setting, so that a recording protocol is possible with only one pass, which can be controlled automatically. A separate test pass is then no longer necessary to determine appropriate parameters.

Advantageously in the context of the method at least one image recording capturing the blood vessel system in the leg region and/or from the heart to the leg region of the patient and/or at least one image recording of the whole body is/are created.

The method is offered in particular when larger body regions, in particular peripheral body regions, are to be captured in the context of an image sequence. Such recordings can for example be recordings of the legs but in some circumstances they can also be recordings, which capture an even larger region, for example from the heart to the legs (including the legs) etc., or, at least essentially, the entire body of the patient.

The invention also relates to a digital subtraction angiography facility, which is configured to implement a method as described above. To this end the facility preferably has a control and/or computation facility, which allows the fully automated operation of the method as required. The control and/or computation facility is therefore configured not only to create the image recordings using an angiography apparatus of the facility, e.g. a C-arm with a radiation source and a detector, but also to trigger the necessary detector advance and to observe and/or define contrast agent diffusion, in particular in the context of a so-called bolus tracking method. The processing of the image recordings, including subtraction, to obtain the final vessel displays for subsequent evaluation by a program means or by the physician, is preferably also carried out fully automatically, optionally as a function of operator defaults for a required type of display or form of recording for subsequent storage. The final recordings can be stored in the control and/or computation facility for subsequent retrieval.

BRIEF DESCRIPTION OF THE DRAWINGS

Further advantages, features and details of the invention will emerge from the exemplary embodiments that follow and from the drawings, in which:

FIG. 4 shows a basic diagram of the implementation of an inventive method with a number of detector position changes and FIG. 5 shows a basic diagram of the implementation of an inventive method when recording parameters are modified during image acquisition.

DETAILED DESCRIPTION OF THE INVENTION

Figure 1:
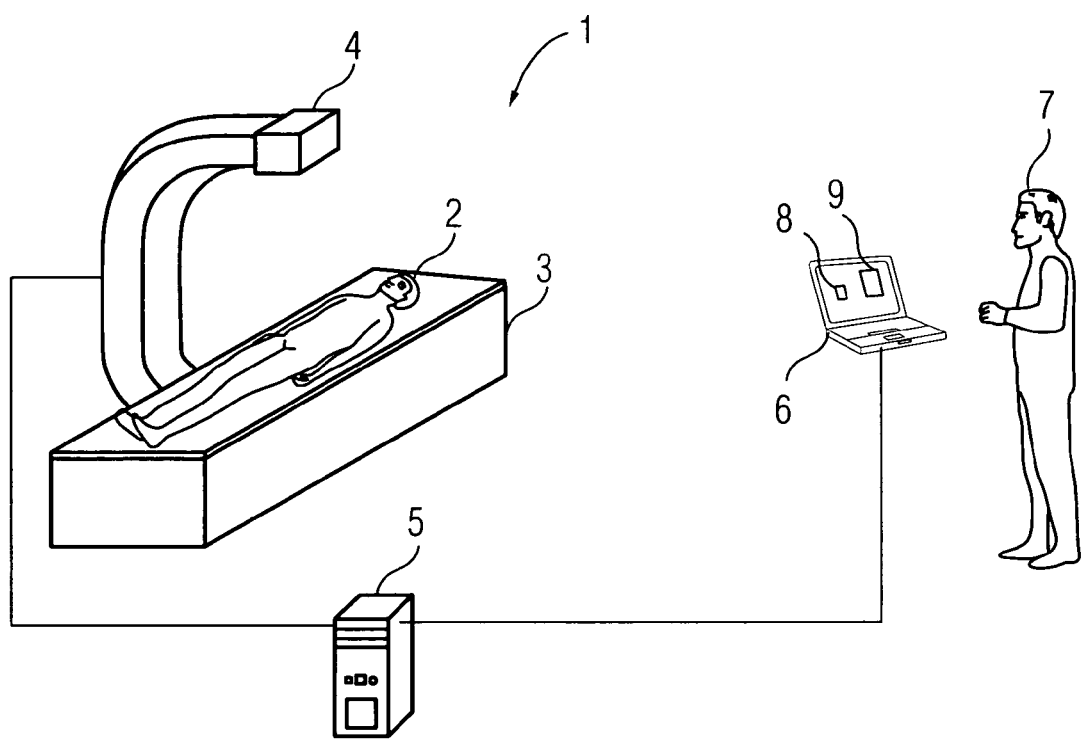
FIG. 1 shows a digital subtraction angiography facility for implementing an inventive method.

FIG. 1 shows a facility 1 for digital subtraction angiography for implementing an inventive method. In the instance shown a patient 2, for whom digital subtraction angiography recordings of the leg region are to be created, is present on a couch 3 of the facility 1. The facility 1 has a C-arm system 4 for recording images, with a radiation source and a detector, which is connected to a control and/or computation facility 5 with an image output means 6, by way of which operator inputs are also possible. In this exemplary embodiment the control and/or computation facility 5 can create the image recordings in a fully automated manner, optionally after an initial start by an operator 7.

This means that, once the operator 7 has triggered image recording once, a recording is first created automatically in a first position of the detector, which is arranged opposite the radiation source of the C-arm system 4. After that a contrast agent is administered to the patient 2, either in a fully automated manner or manually, whereupon a further recording is produced in the same detector position. The control and/or computation facility 5 hereby utilizes an automatic bolus tracking method, in order to implement an automated detector advance when the contrast agent reaches or will soon reach a specific front region of the detector or the image recording region. The image data of the front region, for which image recordings were created in the previous position, is then used as a mask for subtraction from image data defined for the correspondingly identical locational position in the next or a subsequent detector position.

It is thus possible according to the invention with the facility 1 for digital subtraction angiography to dispense with the separate mask pass required with previous realizations, since selective data from the fill pass with contrast agent is used for subtraction. The recording of the front detector segment of the facility 1 is also used as required to carry out an analysis and subsequent optimization of the recording parameters, with the result that it is also possible to dispense with a test pass.

The operator 7 can initiate implementation of the inventive method for example by selecting a corresponding start field 8 on the image output means 6, for example by way of the keyboard, a computer mouse or similar.

The image recordings resulting from a subtraction or as intermediate steps for the recordings in the individual detector positions can be displayed as recordings 9 for the purposes of control by the operator 7 during the examination and/or for subsequent evaluation similarly at the output means 6. The image data and further data, which is determined in the context of implementation of the method, can also optionally be stored in the control and/or computation facility 5, for subsequent evaluation by a physician for example or to be sent by way of an intranet or the Internet to further or external computers.

Figure 2:
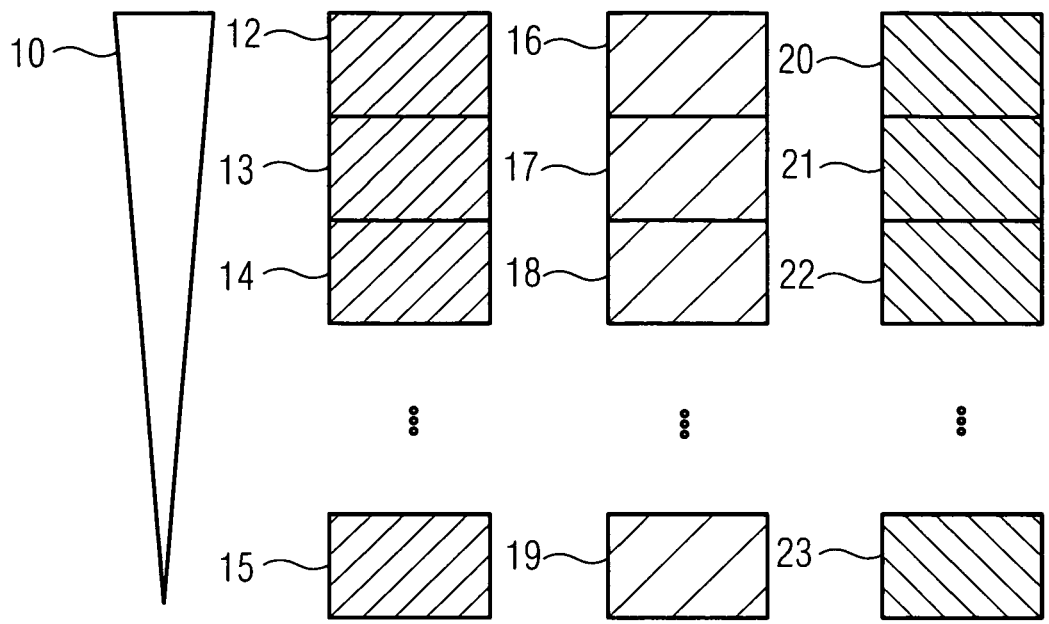
FIGS. 2 and 3 show basic outlines of adaptive subtraction for peripheral vessel display.
Figure 3:
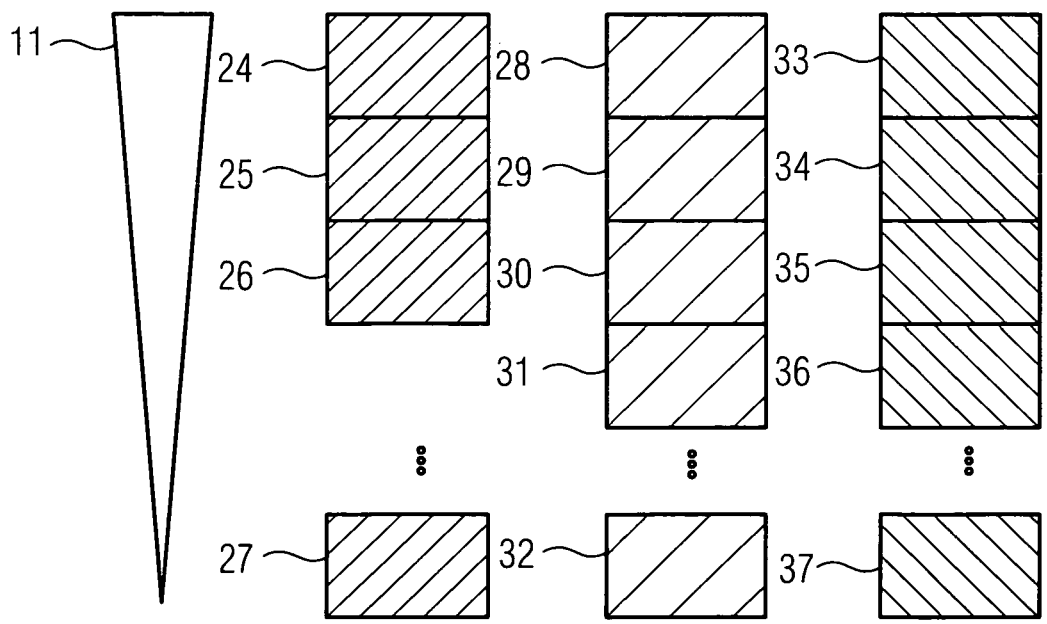

FIGS. 2 and 3 show basic outlines of adaptive subtraction for peripheral vessel display. The arrow 10 in FIG. 2 and the arrow 11 in FIG. 3 symbolize the diffusion of the contrast agent bolus or the direction in which this is observed. The contrast agent can be administered beforehand by a physician or medical personnel or even in a fully automatic manner.

First, as shown in FIG. 2, a series of native image recordings 12, 13, 14 to 15 is created, with further native mask recordings between the native image recording 14 and the image recording 15 not being shown here in order to keep the diagram simple.

After injection of a contrast agent a fill recording, in other words a recording with contrast agent, is created at the respectively identical position (locationally correlated), resulting in the contrast agent recordings 16, 17, 18 and 19, with further recordings (not shown here), as indicated by the dots, again being created between the locations of the contrast agent recordings 18 and 19.

During implementation of the inventive method for subtraction angiography the position of the detector is generally changed a number of times as a function of the flow of the contrast agent, in order to create further recordings to capture an entire required region, with a front recording region, in which there is still no contrast agent present according to the inventive method, being able to be used in each instance as a mask for subsequent recordings.

The locationally correlated recording of corresponding regions allows digital subtraction recordings 20, 21, 22 and 23 (with further recordings in between) to be created respectively by the implementation of adaptive subtraction for peripheral vessel display.

Alternatively it is also possible, as shown in FIG. 3, to create mask recordings 24, 25, 26 and 27, for which the associated contrast agent recordings 28, 29, 30, 31 and 32, were recorded, at least partially, in different positions from the masks. In this instance however it should be ensured that the overlapping of mask and fill recordings is complete, so that the parts of the images cover one another or locational correlations can generally be shown, to which end it must also be possible to assign the parts of the images to one another. The table position for each recording for example can be saved and used here for assignment purposes. It is then possible to obtain digital subtraction recordings 33, 34, 35, 36 and 37.

FIG. 4 shows a basic diagram of the implementation of an inventive method with a number of detector position changes.

The diffusion of the contrast agent bolus in the required recording direction is again shown by the arrow 38, its direction corresponding to the z-direction shown by the arrow 39, also representing the time axis.

The method shown here is based on a division of the detector, used for image recording purposes, into three segments, with native recordings 43 being created for the segments 40, 41 and 42 in a first position.

After the start of the contrast agent injection further recordings 44 are created for the detector segments 40, 41 and 42 in a detector position that is unchanged in relation to the first position. In this first detector position at least one recording respectively of the individual detector segments 40, 41 and 42 is created after contrast agent administration. It is however also possible to create a number of recordings in the first position respectively for one segment 40, 41 and 42.

Bolus tracking is used for the detector advance, with the result that as soon as the contrast agent reaches a region of the body of the patient corresponding to the detector segment 42 in one position, a first detector advance takes place through a third of the detector length. This is followed by one or more recordings 45 in the new second detector position.

The respectively corresponding recordings without contrast agent can be used as mask images for the locationally corresponding recordings or detector elements when recording with contrast agent. This is shown here in each instance by the arrows between the individual recordings, which connect segments 40, 41, 42 of identical position in respect of the contrast agent diffusion direction. For example the recordings for the detector segments 40 and 41 of the native recording 43 can be used as masks for the images for the corresponding detector elements after the start of contrast agent injection, resulting in the image recordings 44. The finer hatching in this diagram is to show the mask recordings, the less fine hatching the fill image recordings. The recording for the detector segment 42 of the image recording 44 can accordingly be used for the image recording 45 as a mask for the detector segment 41 or for the image recording 46 created with a subsequent position change as a mask for the detector segment 40, etc. After a further advance of the detector the image recordings 47 of the individual segments 40, 41, 42 are finally obtained in the diagram in FIG. 4, until an abort condition is satisfied.

Bolus tracking is therefore carried out a number of times to displace the detector by a third of its length on that basis, whereupon one or more recordings are again created in the new position. Locationally corresponding detector elements or the corresponding image data respectively is/are then used for subtraction purposes. This method is repeated until acquisition is completed.

FIG. 5 shows a basic diagram of the implementation of an inventive method when recording parameters are changed during image acquisition. Contrast agent bolus diffusion is shown here by the arrow 48. The z-direction, in other words the longitudinal axis of the recording system, is shown by the arrow 49, which likewise represents the passage of time.

Native recordings 50 of the individual detector segments 51, 52 and 53 are again created in a first position. After the start of contrast agent injection further recordings 54 are created in the same position, with detector advance taking place as soon as the contrast agent reaches the detector segment 53 or a corresponding region in the vascular system, whereupon further recordings 55 are produced in this new position. The corresponding detector elements are again used respectively for subtraction purposes, as shown here by the arrows between the different recordings of the individual segments 51, 52, 53.

Further detector position changes then result in the recordings 56 and 57.

In the diagram used here only one recording for each detector segment 51, 52 and 53 respectively is shown for the individual positions after displacement of the detector (see also the recordings 55, 56 and 57). Of course a number of recordings can also be created for each of the individual detector segments 51, 52 and 53 or as a whole in the respective position of the detector.

The line 58a shows a modification made here to the acquisition parameters. This modification of the acquisition parameters takes place automatically in the present instance. The position-specific recordings are then created automatically, controlled by a control and/or computation facility of the facility for carrying out digital subtraction angiography, for a transition region, in a parallel manner for the old set of acquisition parameters and for the new set of acquisition parameters respectively. This means that in the present instance at least one further recording 58 is produced, for a detector position, which is identical to the one used for the recording 57, for which however the new recording parameters are already used.

In a subsequent position recordings 59 are then produced, which are again based on the original acquisition parameters, while subsequently in a position that is unchanged in relation to the position used for the recording 59 recordings 60 are created, which are based on the new recording parameters.

After the end of this transition phase or this transition region it is then optionally possible only to create recordings with the new parameters in the next position, starting here with the recordings 61, since recordings with the old parameters are no longer required for carrying out subtraction after the further detector advance.

The existence of other acquisition parameters is indicated in the diagram in each instance by a different hatching. The front region of the recordings (for the detector segment 53) still has no contrast agent, as the advance takes place before the contrast agent is diffused into this region, as is also shown by a different hatching compared with the rear detector segments 51 and 52.

Generally the inventive method has the advantage that it can not only be implemented in a fully automatic manner, so that the required operator actions can be kept to a minimum and also errors are avoided but also that the use of selective data from the fill pass with contrast agent means that there is no need for a separate mask pass. Also there is no need for a test pass, as the recording parameters can be analyzed respectively in and/or for the front detector segment and can then be used as the basis for optimization.

The invention claimed is:

1. A method for creating an image recording of a blood vessel system of a patient using a detector of a medical device, comprising:
    administering a contrast agent;
    recording a first image recording of the blood vessel system in a first image recording region of a first position of the detector;
    observing a diffusion of the contrast agent in a predetermined direction of the first image recording region for determining a current diffusion position;
    moving the detector to a second position in the predetermined direction as a function of the current diffusion position;
    recording a second image recording of the blood vessel system in a second image recording region of the second position of the detector;
    defining a part of the first image recording without the contrast agent recorded in a region between the current diffusion position and an end of the first image recording region as a mask;
    evaluating a locationally correlated part of the second image recording with the contrast agent using the mask for a digital subtraction angiography; and
    creating the image recording by the digital subtraction angiography wherein the detector, the first image recording region or the second image recording region are divided into three equally sized parts, wherein a first part acquires a fill image, a second part observes the contrast agent for determining the diffusion position and a third part acquires the mask.

2. The method as claimed in claim 1, wherein an image recording of the blood vessel system in the first image recording region of the first position of the detector is recorded before administrating the contrast agent.

3. The method as claimed in claim 1, further comprising:
    recording a further third image recording in a further third image recording region of a further third position of the detector;
    moving the detector to a further fourth position in the predetermined direction as a function of a further new current diffusion position;
    recording a further fourth image recording of the blood vessel system in a further fourth image recording region of the further fourth position of the detector;
    defining a part of the further third image recording without the contrast agent recorded in a region between the further new current diffusion position and an end of the further third image recording region as a mask; and
    evaluating a locationally correlated part of the further fourth image recording with the contrast agent using the mask for a digital subtraction angiography.

4. The method as claimed in claim 1, wherein the observation of the diffusion of the contrast agent and the determination of the current diffusion position are carried out automatically by a control device of the medical device.

5. The method as claimed in claim 1, wherein the detector is moved automatically by a control device of the medical device.

6. The method as claimed in claim 1, wherein the image recording is created automatically by a control device of the medical device.

7. The method as claimed in claim 1, wherein the image recording is created after an operator-initiated start.

8. The method as claimed in claim 1, wherein the detector, the first image recording region, or the second image recording region is divided discretely or continuously.

9. The method as claimed in claim 1, wherein a position of the detector is changed by a distance that is a fraction of the number of parts in relation to an overall extension of the detector.

10. The method as claimed in claim 1, wherein the creation of the image recording is terminated when a predetermined region of the blood vessel system of the patient is recorded after moving the position of the detector in steps, or is terminated by an operator, or is terminated when the contrast agent is no longer propagated.

11. The method as claimed in claim 1, wherein a recording parameter is modified during the creation of the image recording.

12. The method as claimed in claim 11,
    wherein an image recording is recorded with the recording parameter before modification,
    wherein a further image recording is recorded with the recording parameter after modification, and
    wherein parts of the image recording and the further image recording with corresponding recording parameters are used for the digital subtraction angiography respectively.

13. The method as claimed in claim 1, wherein an image recording parameter is analyzed and optimized by the mask.

14. A medical device for creating an image recording of a blood vessel system of a patient, comprising:
    a detector that:
        records a first image recording of the blood vessel system in a first image recording region of a first position of the detector after administering a contrast agent, and
        records a second image recording of the blood vessel system in a second image recording region of a second position of the detector after administering the contrast agent; and
    a control device that:
        observes a diffusion of the contrast agent in a predetermined direction of the first image recording region for determining a current diffusion position,
        defines a part of the first image recording without the contrast agent recorded in a region between the current diffusion position and an end of the first image recording region as a mask,
        evaluates a locationally correlated part of the second image recording with the contrast agent using the mask for a digital subtraction angiography wherein the detector, the first image recording region or the second image recording region are divided into three equally sized parts, wherein a first part acquires a fill image, a second part observes the contrast agent for determining the diffusion position and a third part acquires the mask, and creates the image recording by the digital subtraction angiography wherein when a recording parameter is modified during creation of an image recording, an image recording is recorded before modification of the recording parameter, and a further image recording is recorded after modification of the recording parameter, wherein the detector is in a same position for both the image recording and the further image recording, and wherein parts of the image recording and the further image recording with corresponding recording parameters are used for the digital subtraction angiography, respectively.

* * * * *